(12) United States Patent
Baxter et al.

(10) Patent No.: US 8,772,670 B2
(45) Date of Patent: Jul. 8, 2014

(54) DUAL GAS LASER CUTTING OF MEDICAL DEVICES

(75) Inventors: Jeffrey W. Baxter, Carlsbad, CA (US); David Mackiewicz, Scotts Valley, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 67 days.

(21) Appl. No.: 13/544,322

(22) Filed: Jul. 9, 2012

(65) Prior Publication Data

US 2012/0273467 A1 Nov. 1, 2012

Related U.S. Application Data

(62) Division of application No. 12/404,586, filed on Mar. 16, 2009, now Pat. No. 8,217,303.

(51) Int. Cl.
| | |
|---|---|
| *B23K 26/14* | (2014.01) |
| *B23K 26/38* | (2014.01) |
| *B23K 26/08* | (2014.01) |
| *B23K 26/42* | (2006.01) |
| *A61F 2/91* | (2013.01) |

(52) U.S. Cl.
CPC ............. *B23K 26/0823* (2013.01); *A61F 2/91* (2013.01); *B23K 26/1405* (2013.01); *B23K 26/147* (2013.01); *B23K 26/1476* (2013.01); *B23K 26/38* (2013.01); *B23K 26/425* (2013.01); *B23K 2201/06* (2013.01); *B23K 2203/08* (2013.01)
USPC ............ 219/121.67; 219/121.72; 219/121.84; 264/400

(58) Field of Classification Search
CPC .................................. B23K 26/14; B23K 26/38
USPC ............ 219/121.67–121.71, 121.72, 121.84; 264/400
See application file for complete search history.

(56) References Cited

U.S. PATENT DOCUMENTS

| | | | | |
|---|---|---|---|---|
| 4,048,464 | A | * | 9/1977 | Gale et al. ................. 219/121.67 |
| 7,786,406 | B2 | * | 8/2010 | Flanagan ................. 219/121.72 |
| 2002/0023905 | A1 | | 2/2002 | Fukaya et al. |
| 2004/0226922 | A1 | | 11/2004 | Flanagan |
| 2008/0296274 | A1 | | 12/2008 | Bialas et al. |

FOREIGN PATENT DOCUMENTS

| | | | |
|---|---|---|---|
| DE | 10249756 A1 | | 5/2004 |
| JP | 02247097 A | * | 10/1990 |
| JP | 08025076 A | * | 1/1996 |
| JP | 11090661 | | 4/1999 |

OTHER PUBLICATIONS

International Search Report issued by the European Patent Office on May 25, 2010.

* cited by examiner

*Primary Examiner* — Samuel M Heinrich
(74) *Attorney, Agent, or Firm* — Fulwider Patton LLP

(57) ABSTRACT

A system prevents oxidation of a laser cut workpiece by utilizing a laser source that utilizes laser source with an inert gas, such as argon or helium, rather than air or oxygen, to create the slots or kerfs which form the pattern cut into the workpiece. The system introduces oxygen gas through the workpiece as it is being laser cut to oxidize any slag or dross created during the laser cutting process. Oxygen or a mixture of oxygen with other gases cools the slag and the workpiece while at the same time oxidizing the slag to either completely burn or partial burn the slag before it strikes an exposed surface of the tubular member.

9 Claims, 1 Drawing Sheet

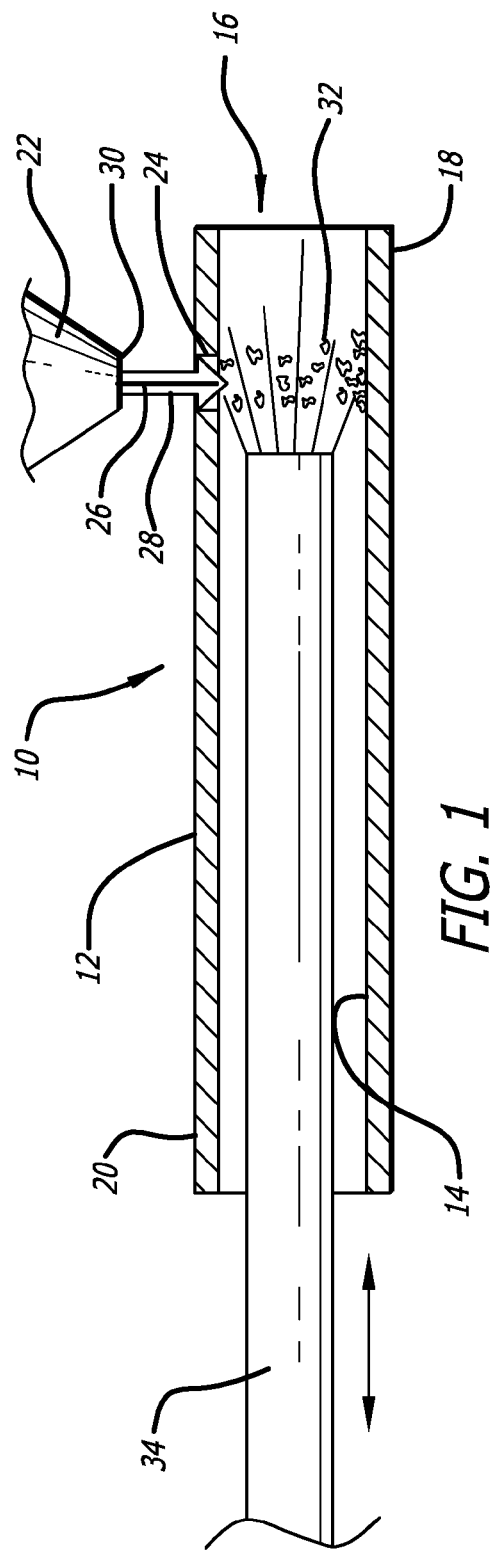
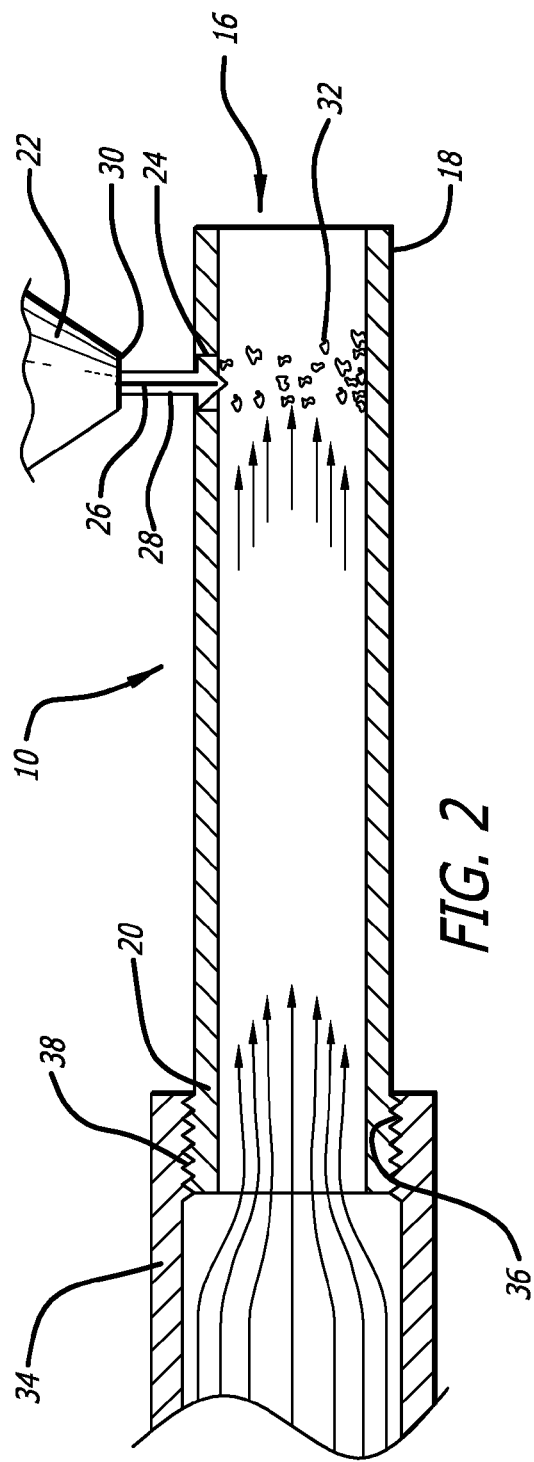

DUAL GAS LASER CUTTING OF MEDICAL DEVICES

CROSS-REFERENCE TO RELATED APPLICATIONS

This is a divisional application based on U.S. Ser. No. 12/404,586, filed on Mar. 16, 2009, the entire contents of which is incorporated herein by reference.

BACKGROUND

The present invention relates generally to methods for laser cutting a hollow workpiece, such as a length of tubing. The present invention is more particularly directed to systems and methods for fabricating medical devices, such as, for example, expandable endoprostheses, commonly known as stents, using a laser apparatus that utilizes an inert gas, instead of air or oxygen, in the cutting process along with oxygen which is introduced during the cutting operation to cool and oxidize slag formed during cutting.

Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the outcome of the procedure and reduce the possibility of restenosis.

Stents are generally cylindrically shaped devices which function to hold open, and sometimes expand, a segment of a blood vessel or other arterial lumen, such as a coronary artery. Stents are usually delivered in a compressed condition to the target site and then deployed at that location into an expanded condition to support the vessel and help maintain it in an open position.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self expanding stent formed from shape memory metals or super elastic nickel titanium alloys (Nitinol), which will automatically expand from a compressed state when the stent is advanced out of the distal end of the delivery catheter into the blood vessel.

Stents can be formed with strut patterns which when expanded have a large amount of open space, but when collapsed have little space between the often tortuously shaped struts forming the stent. One method of making a stent includes laser cutting a tubular member or tubing of suitable material to create the intricate strut patterns which define the structure of the stent. Laser cutting generally provides a precise method for forming these intricate strut patterns in the tubing used to form the stent. Such patterns require the tubing to be cut through one side of the wall of the tubing without cutting through the opposite side of the tubing.

In the past, laser apparatus utilizing pressured air (oxygen) have been used to cut the tubing. Generally, a laser beam locally heats the tubing material while pressurized air is blown through a small coaxial orifice directly onto the heated region in order to create a slot or "kerf" through the wall of the tubing.

Laser cutting of a length of tubing generally begins by focusing a laser beam on a targeted spot on the tubing. The spot is melted and is preferably vaporized, or at least partially vaporized, by the laser beam. Once the laser beam burns through the side wall of the tubing, the beam may continue to strike the opposite side wall of the tubing, and may begin to vaporize, or partially vaporize, the opposite side wall of the tubing. This undesirable burning or partial vaporization of the opposite sidewall is called "burn through" and can result in the weakening of opposite sidewall. In some cases, burn through may result in the workpiece being discarded. The melting and vaporization of the tubing also can form "recast" material, which is material from the tubing that has melted and resolidified on laser-cut surfaces. The recast material, also referred to as "dross" or "slag," contain metal oxides and impurities which are undesirable in the manufacturing process since the recast material must be thoroughly removed from the surface of the stent. Oxidation can make a stent more susceptible to failure (e.g., cracking or fracture) during manufacturing or, if not completely removed, in use. Additionally, recast material can be particularly difficult to remove without damaging the thin struts created by the laser cutting operation. Therefore, both burn through and formation of recast material presents a formidable problem to the stent manufacturer.

The problems of laser cutting self-expanding stents made from a material such as Nitinol are further enhanced when pressurized air or oxygen is used with the laser to create the cut pattern. Because Nitinol is composed of about 50% titanium, a notoriously reactive metal, the titanium readily reacts with the oxygen in the air when heated. As a result, the material expelled during the cutting procedure is predominately comprised of metal oxides, most of which are trapped inside the tubing and adhere to the metallic inner surface of the Nitinol tube. Side walls of the slot or kerf also become oxidized during the cutting process, making the as-cut stent less ductile and thereby more susceptible to cracking or complete fracture during radial expansion or during other subsequent manufacturing steps. As a result, a laser cut Nitinol work piece must be carefully processed by a number of different cycles of chemical treatment, longitudinal expansion, and heat stabilization to achieve the final stent size.

Any remaining slag material which adheres to exposed portions of the tubular member must be removed in order to attain an acceptably smooth surface later during electropolishing. This additional clean up procedure can be achieved through a combination of automated grit blasting, manual grit blasting and chemical removal of material prior to electropolishing. Some methods require the physical removal of the recast material using a reamer or similar equipment and can often damage the thin struts of the stent. While electropolishing procedures can remove some recast material, often the recast material may be so heavily clad on the surface of the stent that not all of the recast material can be removed by this process. Additionally, the electropolishing process will remove material from the struts so it is important that only a small amount of the strut surface is actually removed. For example, if the electropolishing procedure is too long in duration, due to accumulated recast material, portions forming the struts of the stent may have too much material removed, resulting in a damaged or generally weakened stent.

Certain methods have developed to deal with the problem caused by burn through and the formation of recast material on the workpiece. One such method uses a continuous metal wire run through the tubular workpiece to create a "protective barrier" which somewhat helps to prevent the laser beam from striking the opposite sidewall of the tubing. Another system utilizes a liquid flushed through the workpiece as it is being cut. The fluid is usually fed through one end of the tubing and exits through the opposite end of the tubing, along with the newly formed openings in the wall of the tubing created by the laser. The liquid flushes away some of the recast material being created by the vaporization of the tubing. However, the presence of this liquid does not always completely block the laser beam, which can allow the inside wall of the tubing to be heated and damaged. Additionally, the use of liquid requires additional equipment for handling the liquid including discharge equipment, catch basins, waste disposal, and other processing equipment.

Nitinol stents can be laser cut using an inert gas, such as argon or helium, rather than oxygen, to prevent sidewall oxidation which would help prevent cracking or fracturing during subsequent processing. However, laser cutting Nitinol tubing utilizing pressurized argon gas typically cannot produce a finished stent because the expelled melted material formed during the cutting process, i.e., slag, dross or recast material can become "welded" to the inner wall of the tubing. This welded metallic build up could possibly be removed by later processing including reaming, drilling, electric discharge machining and the like.

What has been needed and heretofore unavailable are improved methods for reducing the adverse results caused by slag formation during the cutting operation and removal of recast material which adheres to the inner surface of the workpiece. The present inventions disclosed herein satisfy these and other needs.

SUMMARY OF THE INVENTION

The present invention is directed to systems and methods for laser cutting a tubular workpiece which helps to reduce the number of post-cutting processing steps by preventing oxidation of the sidewall of the workpiece while at the same time oxidizing slag which may be generated during the laser cutting process. The present invention prevents oxidation of the workpiece itself, i.e. the sidewalls of the workpiece, by utilizing a laser apparatus that utilizes laser source with an inert gas, such as argon or helium, rather than air or oxygen, to create the slots or kerfs which form the pattern cut into the workpiece. The absence of oxygen in this part of the cutting process prevents the workpiece from being oxidized during laser cutting. The present invention also utilizes an apparatus to supply of oxygen gas (or an oxygen gas mixture) that can be introduced through the workpiece to oxidize any slag or dross created during the laser cutting process. The presence of the oxygen in the supplied gas cools the slag and the workpiece while at the same time oxidizing the slag to either completely burn or partial burn the slag before it strikes an exposed surface of the tubular member. Thus, the presence of oxygen to this molten metal will help prevent it from aggressively attaching to an exposed surface of the tubular workpiece. The present invention is particularly beneficial in manufacturing intricately shaped devices from a hollow workpiece, such as a stent.

In one aspect of the invention, in the laser cutting process, recast material slag formed during the cutting process is forced through the kerf formed as the laser melts the material and the pressurized inert gas pushes the slag through the inner lumen of the tubular workpiece. As the slag moves towards the inner surface of the tubular member, the flow of oxygen both cools the slag and oxidizes it to either burn it completely or partially so as to prevent the slag from aggressively adhering or welding itself to the exposed surface of the tubular workpiece. Tubing made from Nitinol or nickel-titanium alloys can be laser cut using an inert gas without the risk of the recast material being welded onto the inner surface of the tubular member. During the cutting operation, the expelled molten material (slag) does collect on the inner surface of the tubular workpiece; however, the slag is not strongly affixed or "welded" to the inner surface of the workpiece and can be easily removed by minimal mechanical and/or chemical cleaning. Because the laser source utilizes an inert gas for cutting, the lack of oxygen at the laser cutting site prevents the sidewalls of the tubular member from becoming oxidized, thus allowing the cut workpiece to be processed with little or no need to grit blast tough oxidized material from the sidewalls prior to electropolishing.

The system utilizes an apparatus which supplies a flow of oxygen within the inner lumen of the tubular member. In this fashion, any slag which drips or is propelled into the inner lumen will be cooled and oxidized, or at least partially oxidized, before it has the chance to strike and strongly adhere to an exposed surface of the tubular member. In one aspect of the present invention, the apparatus includes a nozzle which is connected to an oxygen source. This nozzle would be adapted to be placed in the inner lumen of the tubular member or directly mounted onto an end of the tubular member during laser cutting. The nozzle is adapted to provide a sufficient oxygen flow within the inner lumen of the tubular member. In another aspect of the present invention, the nozzle is movable within the inner lumen of the tubular member and can be synchronized with the laser cutting source so that the nozzle is not struck by the laser beam after it cuts through the wall of the tubular member.

After the tubular member has been laser cut, again, there may be a build up of some slag on exposed surfaces of the workpiece. The slag must still be removed from the workpiece prior to electropolishing. The slag could be more easily removed from the workpiece utilizes a variety of mechanical and/or chemical techniques.

These and other advantages of the present invention become more apparent from the following detailed description of the invention, when taken in conjunction with the accompanying exemplary drawings.

BRIEF DESCRIPTION OF THE DRAWINGS

FIG. 1 is a side elevational view, partially in cross section showing a schematic representation of a system and method for cutting a device, such as a stent, from a tubular member using a laser device which utilizes an inert gas to assist in the cutting process, along with a flow of oxygen gas to oxidize or at least partially oxidize any slag which may be generated during the cutting operation; and FIG. 2 is a side elevational view, partially in cross section showing an alternative embodiment of a system and method for a tubular member using a laser device which utilizes an inert gas to assist in the cutting process, along with a flow of oxygen gas to oxidize or at least partially oxidize any slag which may be generated during the cutting operation.

DETAILED DESCRIPTION OF THE PREFERRED EMBODIMENTS

Referring now to the drawing in which reference numerals represent like or corresponding elements across the drawings, a system and method of making a device from a hollow tubular member 10 is generally disclosed. The present invention relates generally to methods for laser cutting a length of hollow tubing, or as is it referred to herein a "tubular member," to form a device, typically a medical device, such as a stent. While most workpieces formed in accordance with the present invention are in the form of a tubular member having a circular cross section, the tubular member could have a non-circular cross section as well. For example, the tubular member could have a rectangular, oval, square, and the like cross section, if desired. Moreover, the invention is not limited to forming stents and has a wide application with respect to other laser cut medical devices and non-medical products, particularly products which require a high precision pattern that is cut utilizing a laser cutting process.

Referring specifically to FIG. 1, in one particular form of the present invention, the method includes providing a tubular member 10 which will be formed into the finished device. The tubular member 10 has wall defined by an outer surface 12 along with an inner surface 14. An inner lumen 16 extends from one end 18 of the tubular member to the other end 20. The tubular member 10 is made from a particular material suitable for the finished device and is to be laser cut, as will be described herein, to generally form the desired pattern and shape of the finished workpiece. The present invention is particularly useful in cutting a tubular member made from a nickel-titanium alloy (Nitinol) or a ternary nickel-titanium alloy such as nickel-titanium-platinum. When a stent is being fabricated, the tubular member will be laser cut to remove portions of the tubular member to create the desired strut patterns of the stent. It should be appreciated that additional processing of the workpiece may be needed after initial laser cutting to achieve the final finished product.

As can be seen in FIG. 1, the tubular member 10 is shown being laser cut by a laser apparatus 22, shown schematically in the drawing figures. The laser cutting apparatus 22 of the present invention utilizes a pressurized inert gas, such as argon or helium, rather than air or oxygen, to create the slots or kerfs 24 extending through the wall of the tubular member 10. Generally, as is schematically depicted in FIG. 1, a laser beam 26 locally heats the tubular member 10 while the pressurized inert gas, depicted by arrow 28, is blown through a small coaxial orifice 30 directly onto the outer surface the heated region in order to create the slots or kerfs 24.

Laser cutting of the tubular member 10 generally begins by focusing a laser beam on a targeted spot on the tubing. The spot is melted by the laser beam while the pressurized inert gas forces the molten material through the wall of the tubular member to form the kerf 24. The tubular member 10 is moved by an automated mechanism (not shown) of the laser cutting apparatus to selectively remove (cut) portions of the wall of the tubular create to create a desired pattern. Once the laser beam burns through the side wall of the tubular member 10, the laser beam could possibly continue to strike the opposite inside surface 14 of the tubular member. In the laser cutting process, recast material or slag 32 is forced as molten metal through the kerf 24 via the pressurized inert gas and can collected as a solid mass becoming "welded" to the inner surface 14 of the tubular member 10.

In order to mitigate the damage that free flowing dross can create to the workpiece, oxygen, or an oxygen mixed gas, is introduced into the inner lumen 16 of the tubular member to cool and vaporize the by oxidization before hitting an exposed surface of the tubular member. Suitable oxygen mixed gases which can be utilized are disclosed below. FIG. 1 shows how the oxygen is introduced into the inner lumen 16 of the tubular member by utilizing a nozzle 34 that is sized to fit within this inner lumen 16. This nozzle 34 is connected to an oxygen supply (not shown) which causes a flow of oxygen to enter the inner lumen 16. This nozzle 34 is designed to be maintained at a safe distance away from the heat zone where the laser beam and pressurized inert gas strike the outer surface 12 to remove portions of the wall. As the laser cuts the wall, any slag which is generated will likely burn through oxidation and will either not adhere to the inner surface 14 or will be only minimally bonded to the surface 14. Theoretically, since molten metal should burn in the presence of pure oxygen, it is desired to burn the slag as much as possible to create a residual byproduct which will not adhere to the surface 14 and can be simply blown out of the inner lumen 16. Accordingly, less post-cutting processing of the workpiece would be required prior to electropolishing.

As is best depicted in FIG. 2, another embodiment of the present invention is shown in which the nozzle 34 is coupled to the tubular member 10 in order to introduce oxygen into the inner lumen 16. In this system, the nozzle can include threads 36 which mate with corresponding threads 38 formed at the end 18 of the tubular member. This end 18 which includes threads 38 could be cut from the finished workpiece after laser cutting is completed. It should be appreciated that other components which are capable of affixing the nozzle 34 to the tubular member could also be used in accordance with the present invention. In this particular system, the automated mechanism of the laser cutting apparatus would move the nozzle 34 with the tubular member as laser cutting is performed.

The pressurized inert gases used with the laser cutting apparatus include argon or helium as these two inert gases are economical and commercially available. However, it should be understood that the laser cutting apparatus could utilize any inert gas to prevent the work piece from oxidizing. Since argon and helium gases are more readily available commercially, these inert gases may serve to be more economical from a cost standpoint.

Generally, the tubular member can be placed in a rotatable collet fixture of a machine-controlled apparatus for positioning the tubular member relative to the laser source. According to machine-encoded instructions, the tubular member can then be rotated and moved longitudinally relative to the laser source which can also be machine-controlled. The laser selectively removes the material from the tubular member by ablation and a pattern is cut into the tubular member. The tubular member is therefore cut into the discrete pattern of the finished workpiece. Further details on how the tubular member can be cut by a laser are found in U.S. Pat. No. 5,759,192 (Saunders) and No. 5,780,807 (Saunders), which have been assigned to Advanced Cardiovascular Systems, Inc. and are incorporated herein by reference in their entirely.

The process of cutting a pattern into the tubular member is automated except for loading and unloading the length of tubing. For example, a pattern can be cut into the tubular member using a CNC-opposing collet fixture for axial rotation of the length of tubular member, in conjunction with CNC X/Y table to move the length of tubular member axially relative to a machine-controlled laser as described. The entire space between collets can be patterned using a Nd:YAG laser set-up. The program for control of the apparatus is dependent on the particular configuration used and the pattern to be ablated in the coding.

The tubular member can be made from a suitable composition of nickel-titanium which is approximately 55% nickel and 45% titanium (by weight) with trace amounts of other elements making up about 0.5% of the composition. It should be appreciated that other compositions of nickel-titanium can be utilized, for example, such as nickel-titanium-platinum, and other metals and alloys. Accordingly, the tubular member could thus be made from binary and ternary nickel-titanium alloys. The tubular member could be made from any material which will be oxidized by an air/oxygen based laser source.

The present invention contemplates the use of pure or near pure oxygen gas as the medium which is introduced into the inner lumen of the tubular member during laser cutting. However, the range of oxygen or oxygen mixed gas which should be capable of burning or oxidizing the generated slag is about from 1% to 100% pure oxygen. For example, oxygen/nitrogen mixture can be used. The range of oxygen/nitrogen mixed gas can be in the range of about 1% oxygen/99% nitrogen to about 99.9% oxygen/0.1% nitrogen. Moreover, other gases could be mixed with oxygen. for example, a blend of helium and oxygen could be used. The range of this mixture can be from about 80% oxygen/20% helium to about 50% oxygen/50% helium. Still other gases could be mixed with the oxygen to improve heat transfer.

While the invention has been illustrated and described herein, in terms of methods for fabricating a medical device, such as an intravascular stent, it will be apparent to those skilled in the art that the systems and methods can be used to manufacture other devices. Further, other modifications and improvements can be made without departing from the scope of the present invention.

We claim:

1. A system for laser cutting a tubular member, comprising:
   a laser source which utilizes a pressurized inert gas to cut the wall of a tubular member; and
   an apparatus for introducing oxygen gas into the inner lumen of the tubular member while the laser source cuts the wall of the tubular member, wherein the apparatus includes a nozzle which is connected to an oxygen source and at least a portion of the nozzle is adapted to be placed within the inner lumen of the tubular member during laser cutting and the system further includes a mechanism for moving the nozzle within the tubular member as the tubular member is being cut.

2. A system for laser cutting a tubular member, comprising:
   a laser source which utilizes a pressurized inert gas to cut the wall of a tubular member; and
   an apparatus for introducing oxygen gas into the inner lumen of the tubular member while the laser source cuts the wall of the tubular member, wherein the apparatus includes a nozzle which is connected to an oxygen source and the nozzle is coupled to the tubular member.

3. The system of claim 2, wherein the tubular member to be cut includes threads for engaging the nozzle.

4. The system of claim 2, wherein the system includes a mechanism for moving the nozzle and tubular piece as the tubular piece is being cut.

5. A method for laser cutting a tubular member, comprising:
   providing a tubular member having a coupling element formed thereon, the tubular member having a wall, an inner surface, an exterior surface and an inner lumen;
   attaching a nozzle which is connected to an oxygen source to the coupling element;
   selectively removing a portion of the wall of the tubular member with a laser device which utilizes a pressurized inert gas in cutting the wall of the tubular member; and
   supplying oxygen gas in the inner lumen of the tubular member while the laser device selectively removes a portion of the wall of the tubular member.

6. The method of claim 5, further including:
   removing the nozzle from the tubular member after the portion of the wall of the tubular member has been selectively removing by the laser device; and
   cutting the coupling element from the tubular member.

7. The method of claim 5, wherein the coupling element is threads formed on the tubular element.

8. A method for laser cutting a tubular member, comprising:
   providing a tubular member having a wall, an inner surface, an exterior surface and an inner lumen;
   placing a nozzle which is connected to an oxygen source in the inner lumen of the tubular member;
   selectively removing a portion of the wall of the tubular member with a laser;
   supplying oxygen gas via the nozzle and oxygen source in the inner lumen of the tubular member while the laser device selectively removes portions of the wall of the tubular member; and
   moving the nozzle in the inner lumen as the laser device selectively removes portions of the tubular member.

9. The method of claim 8, wherein the tubular member is moved as the laser device selectively removes portions of the wall of the tubular member.

* * * * *